(12) United States Patent
Gnoyke

(10) Patent No.: US 7,093,311 B2
(45) Date of Patent: Aug. 22, 2006

(54) PATIENT EXAMINATION SUPPORT SYSTEM

(75) Inventor: Hartmut Gnoyke, Pegnitz (DE)

(73) Assignee: Siemens Aktiengesellschaft, Munich (DE)

( * ) Notice: Subject to any disclaimer, the term of this patent is extended or adjusted under 35 U.S.C. 154(b) by 55 days.

(21) Appl. No.: 10/859,417

(22) Filed: Jun. 2, 2004

(65) Prior Publication Data

US 2004/0261178 A1    Dec. 30, 2004

(30) Foreign Application Priority Data

Jun. 4, 2003    (DE)    ................................ 103 25 299

(51) Int. Cl.
    *A61B 19/00*    (2006.01)
(52) U.S. Cl. ................................ 5/601; 5/600; 378/209
(58) Field of Classification Search .................... 5/601, 5/600; 378/209; 600/415
    See application file for complete search history.

(56) References Cited

U.S. PATENT DOCUMENTS

| | | | | |
|---|---|---|---|---|
| 4,365,341 A * | 12/1982 | Lam | ............................. | 378/65 |
| 4,435,862 A * | 3/1984 | King et al. | ..................... | 5/611 |
| 4,680,790 A * | 7/1987 | Packard et al. | ............. | 379/432 |
| 4,685,159 A * | 8/1987 | Oetiker | ........................... | 5/608 |
| 4,751,754 A * | 6/1988 | Bailey et al. | .................. | 5/611 |
| 4,791,934 A * | 12/1988 | Brunnett | ..................... | 600/429 |
| 5,446,548 A * | 8/1995 | Gerig et al. | ................. | 356/620 |
| 5,515,561 A * | 5/1996 | Suggitt et al. | ................. | 5/607 |
| 5,533,082 A | 7/1996 | Gronemeyer et al. | ......... | 378/20 |
| 5,542,138 A * | 8/1996 | Williams et al. | ............. | 5/658 |
| 5,628,078 A * | 5/1997 | Pennington et al. | ........... | 5/618 |
| 5,754,997 A * | 5/1998 | Lussi et al. | ..................... | 5/618 |
| 5,815,865 A * | 10/1998 | Washburn et al. | ............. | 5/713 |
| 5,861,865 A * | 1/1999 | Anand et al. | ................ | 345/658 |
| 5,864,331 A * | 1/1999 | Anand et al. | ................ | 345/656 |
| 5,926,002 A * | 7/1999 | Cavanaugh et al. | ........ | 318/672 |
| 6,008,598 A * | 12/1999 | Luff et al. | ..................... | 318/16 |
| 6,038,718 A * | 3/2000 | Pennington et al. | ........... | 5/618 |
| 6,106,576 A * | 8/2000 | Fromson | ....................... | 318/16 |
| 6,115,861 A * | 9/2000 | Reeder et al. | .................. | 5/727 |
| 6,279,579 B1 * | 8/2001 | Riaziat et al. | ............... | 128/897 |
| 6,351,678 B1 * | 2/2002 | Borders | ........................ | 700/83 |
| 6,378,152 B1 * | 4/2002 | Washburn et al. | ............. | 5/713 |
| 6,396,224 B1 * | 5/2002 | Luff et al. | ..................... | 318/16 |
| 6,460,209 B1 * | 10/2002 | Reeder et al. | .................. | 5/690 |
| 6,486,792 B1 * | 11/2002 | Moster et al. | ......... | 340/825.19 |
| 6,560,492 B1 * | 5/2003 | Borders | ........................ | 700/17 |
| 6,611,979 B1 * | 9/2003 | Welling et al. | ................. | 5/624 |
| 6,658,680 B1 * | 12/2003 | Osborne et al. | ............... | 5/600 |
| 6,687,935 B1 * | 2/2004 | Reeder et al. | .................. | 5/691 |

(Continued)

FOREIGN PATENT DOCUMENTS

AT    343 266 B    5/1978

(Continued)

OTHER PUBLICATIONS

German Office Action dated Oct. 20, 2005 with English Translation.

*Primary Examiner*—Robert G. Santos
(74) *Attorney, Agent, or Firm*—Brinks Hofer Gilson & Lione

(57) ABSTRACT

A patient examination support system includes a positioning display that displays the patient position required for an examination and/or treatment. Characteristic parameters for the examination and/or treatment of a patient via an X-ray or radiological system are made available at a reduced expense and with substantial reliability, via a preferably remote-controllable positioning display to persons operating the system.

10 Claims, 1 Drawing Sheet

U.S. PATENT DOCUMENTS

| | | | |
|---|---|---|---|
| 6,691,346 B1* | 2/2004 | Osborne et al. | 5/600 |
| 6,780,149 B1* | 8/2004 | Schulte | 600/1 |
| 6,781,517 B1* | 8/2004 | Moster et al. | 340/825.19 |
| 6,880,189 B1* | 4/2005 | Welling et al. | 5/624 |
| 6,952,854 B1* | 10/2005 | Blaustein et al. | 15/22.1 |
| 6,957,461 B1* | 10/2005 | Osborne et al. | 5/618 |
| 6,978,500 B1* | 12/2005 | Osborne et al. | 5/600 |
| 7,010,369 B1* | 3/2006 | Borders et al. | 700/90 |
| 2001/0032362 A1* | 10/2001 | Welling et al. | 5/600 |
| 2002/0002742 A1* | 1/2002 | Osborne et al. | 5/600 |
| 2002/0023652 A1* | 2/2002 | Riaziat et al. | 128/897 |
| 2002/0066142 A1* | 6/2002 | Osborne et al. | 5/600 |
| 2002/0178503 A1* | 12/2002 | Reeder et al. | 5/600 |
| 2003/0115672 A1* | 6/2003 | Newkirk | 5/600 |
| 2004/0034936 A1* | 2/2004 | Welling et al. | 5/624 |
| 2004/0128765 A1* | 7/2004 | Osborne et al. | 5/600 |
| 2004/0133987 A1* | 7/2004 | Reeder et al. | 5/713 |
| 2004/0177445 A1* | 9/2004 | Osborne et al. | 5/600 |
| 2004/0261178 A1* | 12/2004 | Gnoyke | 5/601 |
| 2005/0125897 A1* | 6/2005 | Wyslucha et al. | 5/600 |
| 2006/0021142 A1* | 2/2006 | Hornbach et al. | 5/600 |
| 2006/0021144 A1* | 2/2006 | Hornbach et al. | 5/618 |
| 2006/0021145 A1* | 2/2006 | Hornbach et al. | 5/618 |
| 2006/0026765 A1* | 2/2006 | Hornbach et al. | 5/618 |

FOREIGN PATENT DOCUMENTS

| | | |
|---|---|---|
| DE | 21 58 457 A1 | 5/1973 |
| DE | 42 02 302 C2 | 6/1999 |
| DE | 10 108 549 | 3/2002 |
| DE | 101 08 549 A1 | 3/2002 |
| DE | 10 151 236 | 5/2003 |

* cited by examiner

PATIENT EXAMINATION SUPPORT SYSTEM

BACKGROUND

The invention relates, in general, to clinical patient tables or support systems, and more particularly to a patient examination tabletop for a diagnosis and/or treatment system, such as a computed tomography or CT system.

One such patient examination support system is known for instance from German Patent Disclosure DE 101 08 549 A1.

During an examination of a patient by means of a tomography system, the patient can take various positions on a patient examination tabletop, characterized for instance by the designations "head first", "feet first", "face up", and "face down". Medical professionals, such as doctors, nurses, technicians, or the like, typically receive instructions on positioning the patient that are required for the examination in writing on a request form. Passing or communicating this information on to an x-ray technician is one possible source of error. In a most favorable case, an error may cause only additional expenditure of time for a required repositioning of the patient. If the error is discovered too late, however, the result can be an imaging examination that does not contribute to the diagnosis.

OBJECT AND SUMMARY

The present invention is defined by the appended claims. This description summarizes some aspects of the present embodiments and should not be used to limit the claims.

One object is to disclose a patient examination support system for a diagnosis and/or treatment system which makes correct positioning of the patient for the examination and/or treatment easier.

Another object is to disclose a patient examination support system having a positioning display, which displays the patient position required for the examination and/or treatment to the persons or users carrying out the examination and/or treatment and/or to the patient. The positioning display can be integrated with the patient examination tabletop, the diagnosis and/or treatment system, in particular a CT system, or an arbitrary display or control unit.

The patient examination tabletop is preferably limited to only a few display elements, particularly with displays in symbol form. Such displays are in particular displays for the aforementioned positions, that is, "head first", "feet first", "face up", and "face down".

In one embodiment, the patient examination tabletop may be linked in an advantageous way with a patient data system, in particular radiology information system. This data linkage may keep a likelihood of error in positioning the patient on the tabletop substantially slight. However, it can also be provided that instead of inputting the desired patient positioning via a data processing system, inputting can be done and/or an input can be changed on the spot.

The positioning display makes use of any technology that is conventional for display elements. Display elements that can be lighted with light-emitting diodes (LEDs) are preferably employed.

One advantageous feature resides in particular in the fact that basic parameters for the examination and/or treatment of a patient, particularly by means of an x-ray or radiological system, are made available by means of a preferably remote-controllable display at the least possible expense and with substantial reliability to the persons operating the system.

Illustrative and exemplary embodiments of the invention are described in further detail below with reference to and in conjunction with the figures.

DETAILED DESCRIPTION

Figure 1:
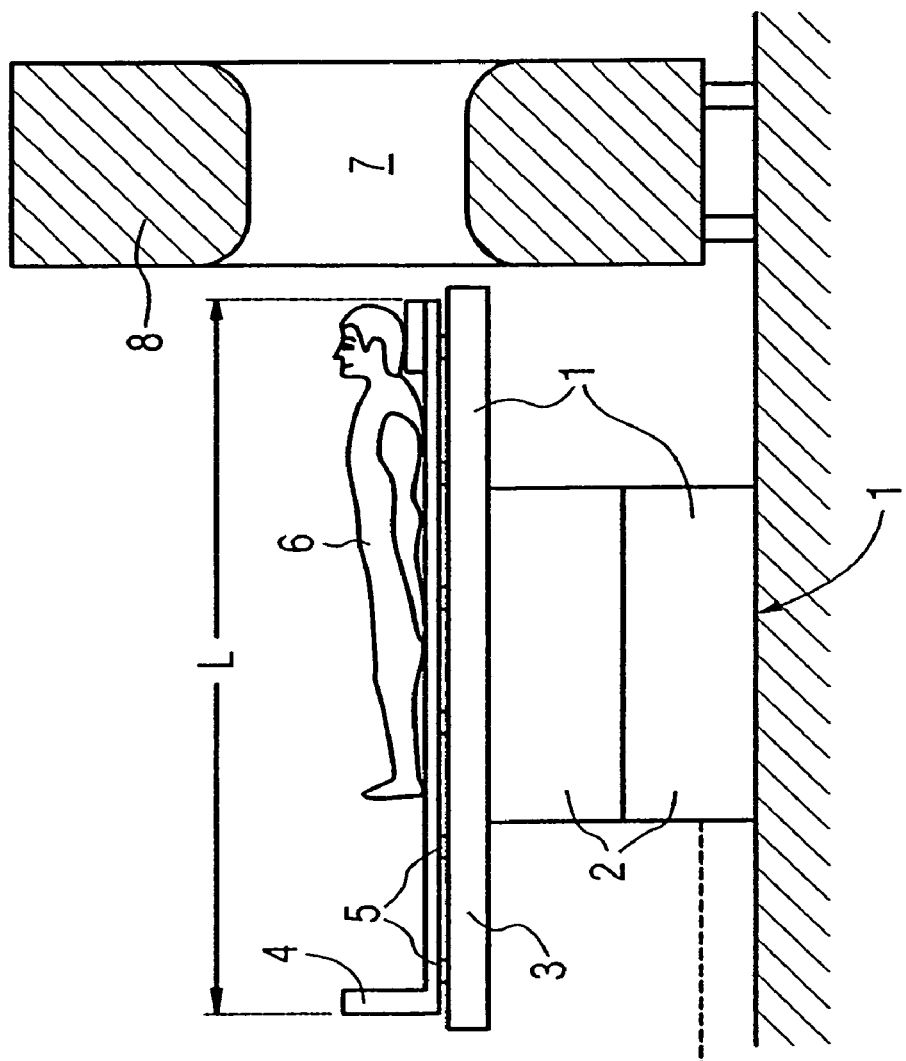
FIG. 1 illustrates an embodiment of a patient examination support system with a positioning display.
Figure 1:
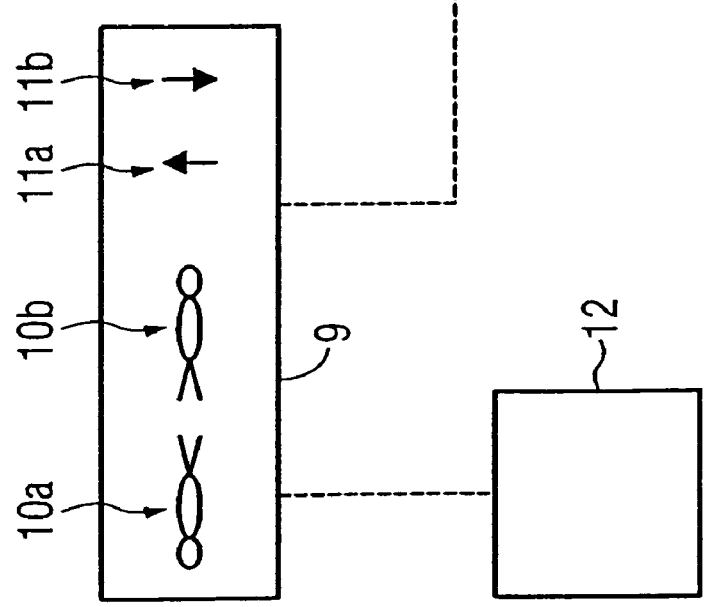

A patient examination support system 1 includes a vertically adjustable support unit 2 and a platform 3, disposed on it, of a length L, on which a tabletop 4 is supported longitudinally and operably displaceable by means of bearing elements 5. The patient examination tabletop may alternatively be a cot or gurney. The longitudinally displaceable support of the tabletop 4 serves the purpose of shifting a patient 6 into an examination area 7 of an examination or diagnosis system 8, in this case a CT system, and/or moving the patient through the examination area 7 at a defined rate of advance. The patient 6 is shown in the drawing in the "head first" position on the table 4.

To display the position required for the treatment of the patient 6 on the tabletop 4 of the imaging diagnosis system 8, a positioning display 9 with four display elements 10a, 10b, 11a, 11b is provided. The display elements 10a, 10b may symbolize the patient positions "head first" and "feet first", respectively. The display elements 11a, 11b may indicate the positions "face up" and "face down", respectively, required for the examination. Before the examination of the patient 6, an appropriate one of the display elements 10a, 10b and 11a, 11b is lighted by means of LED technology. The data for triggering the positioning display 9 are transmitted, by means of a data connection system represented in dashed lines, which in general comprises a plurality of data systems, from a patient data system 12, which either includes or is identical to a radiology information system. A further data connection system, also indicated by dashed lines, between the positioning display 9 and the patient examination support system 1 is optionally provided and serves for instance to transmit readiness reports and/or error reports to the positioning display 9.

In another embodiment, the display elements 10a, 10b, 11a, 11b are preferably not triggered directly by the radiology information system. Instead, the required data made available may be picked up from a central computer or a computing controller, not shown, of the diagnosis system 8 serving as an imaging system; with this information, via other devices, also not shown in further detail, the central computer may trigger the display elements 10a, 10b, 11a, 11b, which are embodied as light-emitting diodes (LEDs). The computing controller operably includes a memory, and software stored in the memory to monitor the patient examination support system and trigger the corresponding display elements when treating or diagnosing the patient.

The invention claimed is:

1. A patient examination support system comprising:
  a tabletop; and
  a positioning display that displays an iconic display element representing a patient position, the patient position being an intended position on the tabletop established for a diagnosis and/or treatment system.

2. The patient examination support system of claim 1, wherein a computed tomography system is provided as the diagnosis system.

3. The patient examination support system of claim 1, wherein in the positioning display includes at least one of a "head first" display element, a "feet first" display element or combinations thereof.

4. The patient examination support system of claim 1, wherein the positioning display includes at least one of a "face up" display element, a "face down" display element or combinations thereof.

5. The patient examination support system of claim 4, wherein the positioning display includes at least one of a "head first" display element, a "feet first" display element or combinations thereof.

6. The patient examination support system of claim 1, wherein the positioning display is located adjacent to the tabletop.

7. The patient examination support system of claim 1, wherein the positioning display is linked with a patient data system.

8. The patient examination support system of claim 1, wherein the positioning display has a light-emitting diode.

9. The patient examination support system of claim 7, wherein the patient data system communicates at least one of readiness and error reports between the patient examination support system and the positioning display.

10. The patient examination support system of claim 7, the patient data system further comprising a computing controller that triggers the display elements embodied as LEDs in response to the positioning of the patient on the examination tabletop.

* * * * *